United States Patent
Niculescu-Mizil et al.

(10) Patent No.: US 10,733,722 B2
(45) Date of Patent: Aug. 4, 2020

(54) RECONSTRUCTOR AND CONTRASTOR FOR ANOMALY DETECTION

(71) Applicant: NEC Laboratories America, Inc., Princeton, NJ (US)

(72) Inventors: Alexandru Niculescu-Mizil, Plainsboro, NJ (US); Eric Cosatto, Red Bank, NJ (US); Felix Wu, Ithaca, NY (US)

(73) Assignee: NEC Corporation (JP)

( * ) Notice: Subject to any disclaimer, the term of this patent is extended or adjusted under 35 U.S.C. 154(b) by 155 days.

(21) Appl. No.: 15/983,342

(22) Filed: May 18, 2018

(65) Prior Publication Data
US 2018/0374207 A1 Dec. 27, 2018

Related U.S. Application Data

(60) Provisional application No. 62/525,291, filed on Jun. 27, 2017.

(51) Int. Cl.
*G06T 7/00* (2017.01)
*H04N 19/132* (2014.01)
(Continued)

(52) U.S. Cl.
CPC ............ *G06T 7/0008* (2013.01); *G06T 7/001* (2013.01); *G06T 7/0014* (2013.01); *G06T 11/008* (2013.01); *G06T 11/206* (2013.01); *G16H 20/30* (2018.01); *G16H 30/40* (2018.01); *G16H 50/20* (2018.01); *G16H 50/70* (2018.01); *H04N 19/132* (2014.11); *H04N 19/17* (2014.11); *G06T 2207/10032* (2013.01); *G06T 2207/10044* (2013.01); *G06T 2207/10048* (2013.01); *G06T 2207/10081* (2013.01);
(Continued)

(58) Field of Classification Search
CPC ..... G06T 7/0008; G06T 7/001; G06T 7/0014; G06T 11/008; G06T 11/206; H04N 19/132; H04N 19/17; G16H 50/70; G16H 50/20; G16H 20/30; G16H 30/40
See application file for complete search history.

(56) References Cited

U.S. PATENT DOCUMENTS

2017/0076224 A1* 3/2017 Munawar ............... G06N 3/084

OTHER PUBLICATIONS

Van Den Oord, "Conditional Image Generation with PixelCNN Decoders", Advances in Neural Information Processing Systems, Jun. 2016, pp. 1-13.
(Continued)

*Primary Examiner* — Leon Flores
(74) *Attorney, Agent, or Firm* — Joseph Kolodka

(57) ABSTRACT

Systems and methods for detecting and correcting defective products include capturing at least one image of a product with at least one image sensor to generate an original image of the product. An encoder encodes portions of an image extracted from the original image to generate feature space vectors. A decoder decodes the feature space vectors to reconstruct the portions of the image into reconstructed portions by predicting defect-free structural features in each of the portions according to hidden layers trained to predict defect-free products. Each of the reconstructed portions are merged into a reconstructed image of a defect-free representation of the product. The reconstructed image is communicated to a contrastor to detect anomalies indicating defects in the product.

18 Claims, 8 Drawing Sheets

(51) Int. Cl.
    *H04N 19/17* (2014.01)
    *G16H 50/70* (2018.01)
    *G16H 50/20* (2018.01)
    *G06T 11/20* (2006.01)
    *G16H 20/30* (2018.01)
    *G16H 30/40* (2018.01)
    *G06T 11/00* (2006.01)

(52) U.S. Cl.
    CPC ............... *G06T 2207/10088* (2013.01); *G06T 2207/10104* (2013.01); *G06T 2207/10116* (2013.01); *G06T 2207/10132* (2013.01); *G06T 2207/20081* (2013.01); *G06T 2207/20084* (2013.01)

(56) References Cited

OTHER PUBLICATIONS

Sakurada, "Anomaly Detection Using Autoencoders with Nonlinear Dimensionality Reduction", Proceedings of the MLSDA 2014 2nd Workshop on Machine Learning for Sensory Data Analysis. ACM, Dec. 2014, pp. 1-8.

Pathak, "Context Encoders: Feature Learning by Inpainting." CVPR, Apr. 2016, pp. 2537-2544.

Yeh, "Semantic Image Inpainting with Perceptual and Contextual Losses." arXiv:1607.07539, Jul. 2016, pp. 1-19.

An, "Variational Autoencoder Based Anomaly Detection Using Reconstruction Probability", Special Lecture on IE, Dec. 2015, pp. 1-18.

Schlegl, "Unsupervised Anomaly Detection with Generative Adversarial Networks to Guide Marker Discovery", IPMI, Mar. 2017, pp. 1-12.

\* cited by examiner

```
┌─────────────────────────────────────────────────────────────┐
│ Extract an image patch from a location on an original       │
│ image of an item and partially mask the image patch         │
│                          801                                │
└─────────────────────────────────────────────────────────────┘
                              │
                              ▼
┌─────────────────────────────────────────────────────────────┐
│ encode the partially masked image patch by transforming     │
│ the partially masked image patch to a feature space vector  │
│ using one or more hidden layers of an encoder               │
│                          802                                │
└─────────────────────────────────────────────────────────────┘
                              │
                              ▼
┌─────────────────────────────────────────────────────────────┐
│ Reconstruct the partially masked image patch of the item    │
│ by decoding the feature space vector into a reconstructed   │
│ patch using one or more hidden layers of a decoder          │
│                          803                                │
└─────────────────────────────────────────────────────────────┘
                              │
                              ▼
┌─────────────────────────────────────────────────────────────┐
│ Merge the reconstructed patch into a corresponding location │
│ of the locations on the original image to generate a        │
│ reconstructed image                                         │
│                          804                                │
└─────────────────────────────────────────────────────────────┘
                              │
                              ▼
┌─────────────────────────────────────────────────────────────┐
│ Contrast the reconstructed image with the original to       │
│ generate an anomaly map that indicates anomalies at         │
│ locations of differences between the reconstructed image    │
│ and the original image                                      │
│                          805                                │
└─────────────────────────────────────────────────────────────┘
                              │
                              ▼
┌─────────────────────────────────────────────────────────────┐
│ Tag anomalies on the anomaly map to indicate possible       │
│ anomalies in the item corresponding to the differences      │
│ between the reconstructed image and the original image      │
│                          806                                │
└─────────────────────────────────────────────────────────────┘
                              │
                              ▼
┌─────────────────────────────────────────────────────────────┐
│               Automatically correct the anomalies           │
│                          807                                │
└─────────────────────────────────────────────────────────────┘
```

FIG. 8

RECONSTRUCTOR AND CONTRASTOR FOR ANOMALY DETECTION

RELATED APPLICATION INFORMATION

This application claims priority to 62/525,291, filed on Jun. 27, 2017, incorporated herein by reference in its entirety. This application is related to an application entitled "RECONSTRUCTOR AND CONTRASTOR SYSTEM FOR MEDICAL ANOMALY DETECTION", and which is incorporated by reference herein in its entirety.

BACKGROUND

Technical Field

The present invention relates to anomaly detection and more particularly reconstructors and contrastors for anomaly detection applications.

Description of the Related Art

Defects and anomalies appear in products prior to shipment of those products to customers. The defects and anomalies can occur in several ways, in varying frequency and of diverse types depending on the product in question and how it was made. However, the defective products generally do not meet a standard to satisfy a customer due to the defects and anomalies.

Thus, removing the products from a shipment can prevent customer dissatisfaction and ensure a consistent product quality. However, recognizing which products contain defects can be difficult because examples of defective products, especially products with particular types of defects, can be relatively rare.

SUMMARY

According to an aspect of the present principles, a method is provided for detecting and correcting defective products. The method includes capturing at least one image of a product with at least one image sensor to generate an original image of the product. An encoder encodes each of at least one portion of an image extracted from the original image to generate a feature space vector. A decoder decodes the feature space vector to reconstruct the at least one portion of the image into a corresponding at least one reconstructed portion by predicting defect-free structural features in each of the at least one portion according to hidden layers trained to predict defect-free products. Each of the at least one reconstructed portion are merged into a reconstructed image of a defect-free representation of the product. The reconstructed image is communicated to a contrastor to detect anomalies indicating defects in the product.

According to another aspect of the present principles, a method is provided for detecting and correcting defective products. The method includes extracting, with an image patch extractor, portions of an original image of a product. The original image is reconstructed with a reconstructor, including: encoding, with an encoder, each of at least one portion of an image extracted from the original image to generate a feature space vector, and decoding, with a decoder, the feature space vector to reconstruct the at least one portion of the image into a corresponding at least one reconstructed portion by predicting defect-free structural features in each of the at least one portion according to hidden layers trained to predict defect-free products. The portions into the original image are merged with an image merging module to generate a reconstructed image. The original image of the product is contrasted contrasting, with a contrastor, with the reconstructed image to generate an anomaly map indicating locations of difference between the original image and the reconstructed image. The locations of difference are tagged as anomalies with an anomaly tagging device corresponding to defects on the product. An operator is notified automatically with a display of the anomalies.

According to another aspect of the present principles, a system is provided for detecting and correcting defective products. The system includes at least one image sensor for capturing at least one image of a product to generate an original image of the product. A reconstructor reconstructs an original image of a product by reconstructing portions of the original image to be a defectless representation of the portions of the product, the reconstructor including: an encoder to encode each of at least one portion of an image extracted from the original image to generate a feature space vector, and a decoder to decode the feature space vector to reconstruct the at least one portion of the image into a corresponding at least one reconstructed portion by predicting defect-free structural features in each of the at least one portion according to hidden layers trained to predict defect-free products. An image merging module merges each of the at least one reconstructed portion into a reconstructed image of a defect-free representation of the product. An anomaly correction system automatically discards the product according to the tagged anomalies.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 8 is a flow diagram illustrating a system/method for detecting defects and anomalies with a reconstructor and contrastor, in accordance with the present principles.

DETAILED DESCRIPTION OF PREFERRED EMBODIMENTS

Figure 1:
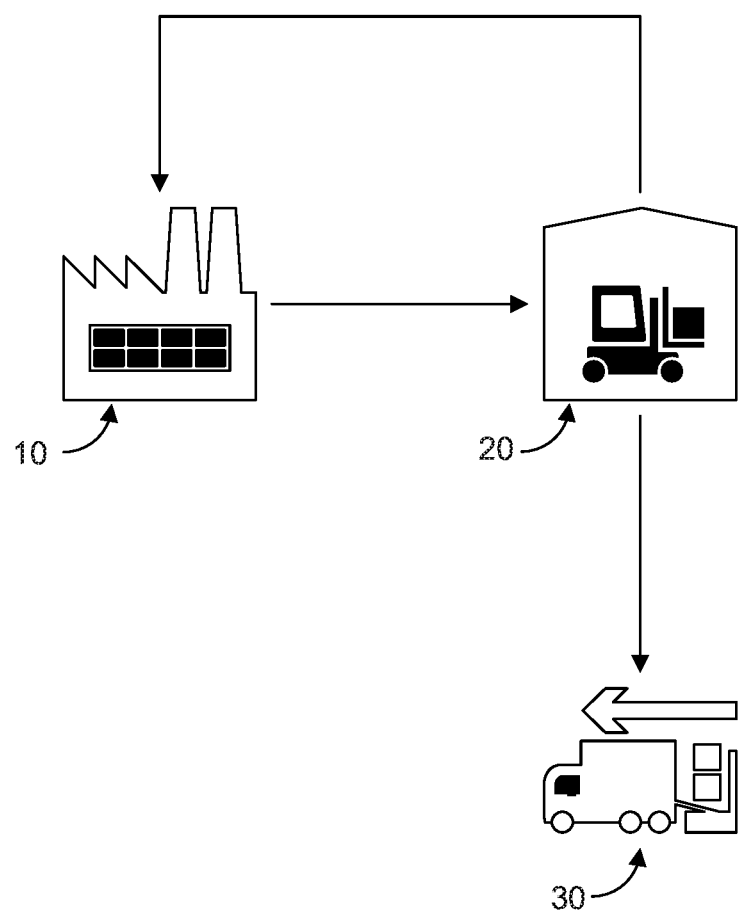
FIG. 1 is a block/flow diagram illustrating a high-level system/method for correcting defective products, in accordance with the present principles.

In accordance with the present principles, systems and methods are provided for anomaly detecting. In particularly useful embodiments, systems and methods can be configured to correct defects in products, such as, e.g., manufactured products.

In one embodiment, a product is inspected for defects using a reconstructor and contrastor. The reconstructor can include an encoder-decoder arrangement employed to reconstruct images of a product containing defects. The encoder-decoder arrangement is trained from examples that contain no defects. Thus, the encoder-decoder arrangement will use an incomplete image of the product, and reconstruct the image according to the defectless training. As a result, a reconstructed image of the product can be produced where the reconstructed image depicts the product having no defects.

The contrastor can then determine a difference between the reconstructed image and an original image of the product. If there is a substantial difference between the original image and the reconstructed image, then the product is considered not defectless. In other words, by failing to match a defectless reconstructed image of the product, it can be determined that the product does contain some anomaly or defect.

Because the systems and methods employed to determine if a product fails to match a defectless reconstruction, an encoder-decoder arrangement can be trained with only normal, defectless images of the product. Thus, training samples can be found in abundance, and thus training the encoder-decoder arrangement can be cheap and efficient.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Referring now in detail to the figures in which like numerals represent the same or similar elements and initially to FIG. 1, a high-level system/method for correcting defective products is illustratively depicted in accordance with one embodiment of the present principles.

In one embodiment, a manufacturing plant 10 manufactures products. The manufactured products may be any physical product. The manufactured products can sometimes be manufactured with defects. Thus, the manufactured products can be sent to a quality assurance system 20.

The quality assurance system 20 inspects the manufactured products to ensure that the products live up to quality standards with respect to issues such as defects and anomalies in the products. Such defects can include visual defects, such as, e.g., cracks, holes, protrusions, discolorations, or any feature that is not part of the original design of the product. The quality assurance system 20 can include an automated system for performing the inspections, such as, e.g., an automated visual system including a camera. However, other inspection systems can be used, including, e.g., radar, infrared, ultrasound, or other detection methods. Based on results, the quality assurance system 20 can automatically take steps to correct the product defects. Such steps can include, e.g., discarding the defecting product, automatically listing the product as defective and requiring refurbishment, alerting an operator to the defect, or any other corrective action.

According to an aspect of the present invention, the corrective action can include listing the product as defective and sending the product back to the manufacturing plant 10 to be recycled or refurbished. However, if the product is not defective, the product can be forwarded to a shipping and packaging system 30 to be sent to a customer.

Figure 2:
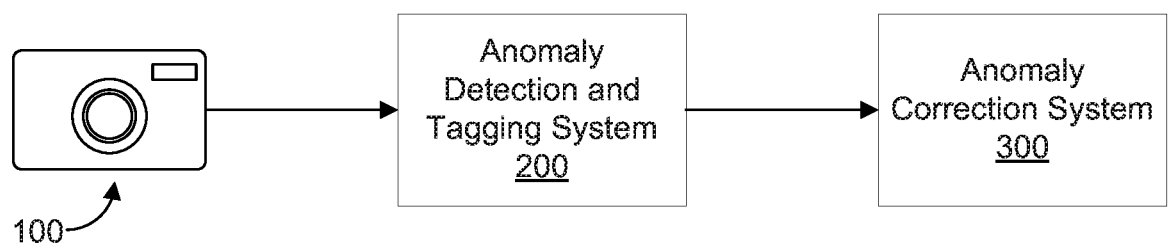
FIG. 2 is a block/flow diagram illustrating a system/method for detecting and correcting defects and anomalies, in accordance with the present principles.

Referring now to FIG. 2, a system/method for detecting and correcting defects and anomalies is illustratively depicted in accordance with an embodiment of the present principles.

According to aspects of the present invention, defects and anomalies in an item are captured by an imaging device 100. The imaging device 100 captures images of an item for analysis to facilitate recognizing defects and anomalies. For example, the imaging device 100 can include, e.g., a camera device or multiple camera devices for capturing images of either the entire item or a portion of the item. Accordingly, multiple imaging devices 100 can be used to concurrently capture images of the item from multiple perspectives. Thus, the entirety of the item, such as, e.g., an entire surface, or for suitable imaging devices 100, an entirety of the depth (as can be the case for imaging devices 100 including, e.g., magnetic resonance imaging (MRI) or computer aided tomography, etc.) can be captured by the imaging device 100. Alternatively, a single imaging device 100 can be used, and the item and the imaging device 100 can be moved relative to each other to capture images from multiple perspectives by, e.g., conveyor, gimbal, or moving stage. The imaging device 100 can also include, e.g., an infrared sensor, a radar sensor, an ultrasound sensor, a light detection and ranging (LIDAR) sensor, among others. Thus, the imaging device 100 can generate an image of the item for analysis.

The image can then be analyzed by an anomaly detection and tagging system 200. The anomaly detection and tagging system 200 process the image to recognize the presence of any potential anomalies with the item according to the image from the imaging device 100. Here, an anomaly is considered to be a feature of the item, as depicted in the image, that deviates from what is usually present at that location of the item. For example, the anomaly detection and tagging system 200 can compare the image of the item to defectless items. Therefore, when the anomaly detection and tagging system 200 analyzes an image of an item that is different from the a defectless item, the anomaly detection and tagging system 200 will determine where in the image and on the item the difference is from the defectless item. The anomaly detection and tagging system 200 can then tag the feature of the item that is different from the defectless item as a potential anomaly or defect.

Information regarding the tagged anomaly can then be provided to an anomaly correction system 300 to take corrective action. The corrective action can depend on the severity of the defects. For example, if the item is a manufactured product, the production line may be stopped, or the item may be discarded or otherwise removed for recycling or refurbishment. A threshold may be used as well, such that if a threshold number of anomalies are tagged, more drastic action may be taken. For example, if the item is a manufactured product, reaching a first threshold number of anomalies can result in the item being discarded, while reaching a second threshold can result in a halting of the entire production line. Alternatively, or in addition, the anomaly correction system 300 can include a notification device to notify an operator of the item having tagged anomalies.

Figure 3:
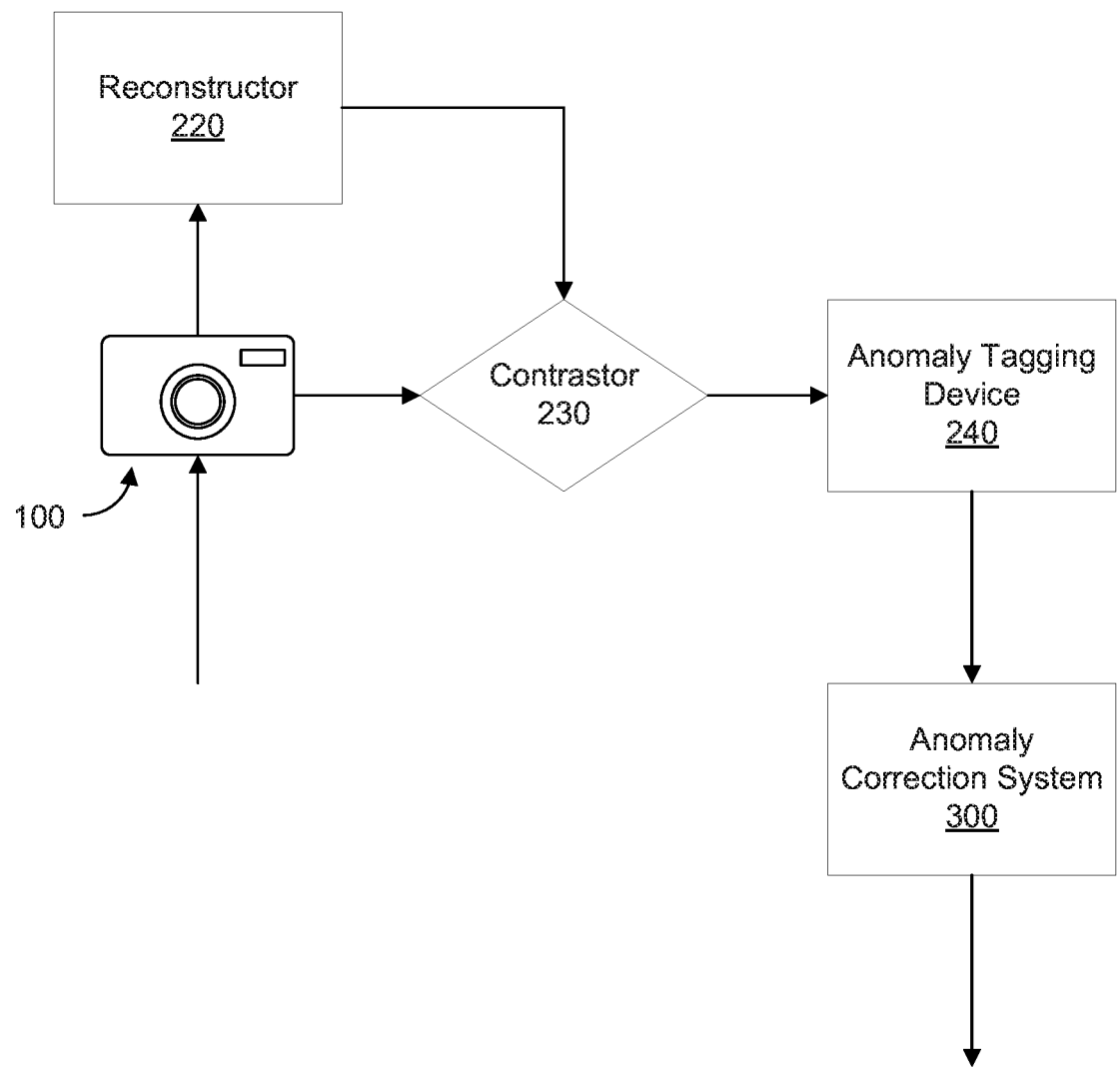
FIG. 3 is a block/flow diagram illustrating a system/method for detecting and correcting defects and anomalies using a reconstructor and contrastor, in accordance with the present principles.

Referring now to FIG. 3, a system/method for detecting and correcting defects and anomalies using a reconstructor and contrastor is illustratively depicted in accordance with the present principles.

According to aspects of the present invention, an image of an item taken by an imaging device 100 can be provided to both a reconstructor 220 and a contrastor 230. The reconstructor 220 can receive the image of the item, e.g., in a memory or storage, and generate a reconstructed image of the item that does not include any defects or anomalies such that the reconstructed image can be contrasted with the original image at the contrastor 230.

The reconstructor 220 will receive the image of the item and reconstruct the image to remove any defects or anomalies. For example, the reconstructor can divide the image in multiple smaller portions of the image, partially mask a region in each smaller portion, and reconstruct each portion. However, other methods of reconstructing the image are contemplated. The reconstructor 220 can include, e.g., a processor to perform reconstruction on the image stored in a memory, such as, e.g., a storage, a random access memory (RAM), a buffer, or a cache, among others. The reconstructor 220 will, therefore, generate with the reconstructed image, a representation of the item that has no defects or anomalies. The reconstructed image can be stored or cached in a storage device, such as, e.g. a RAM, a buffer or a cache.

The reconstructed image will then be provided to the contrastor 230 along with the original image from the imaging device 100. The contrastor 230 can then compare the reconstructed image with the original image. Because the reconstructed image is a defectless representation of the item, any differences between the reconstructed image and the original image will be detected by the contrastor 230. Similar to the reconstructor 220, the contrastor 230 can include, e.g., a processor, to perform the contrasting, and a storage, such as, e.g., a RAM, buffer or cache, to temporarily or permanently store the original image and the reconstructed image.

The contrastor 230 will then provide data regarding the detected difference to an anomaly tagging device 240. The anomaly tagging device 240 will use data regarding the locations of difference between the reconstructed image and the original image to identify anomalies. Thus, the anomaly tagging device 240 can generate a tagged image of the item with anomalies identified and tagged.

The tagged image can be used by the anomaly correction system 300 to take corrective action regarding the anomalies, as described above. For example, the anomaly correction system 300 can, e.g., automatically determine that an item should be discarded if it has a certain number of anomalies. Alternatively, the anomaly correction system 300 can automatically determine that an item should be discarded if it has any anomalies, or that the item can be sent back to manufacturing to be refurbished or recycled. The anomaly correction system 300 can even, e.g., automatically determine that an entire production line should be stopped if an item with anomalies is found, or if a certain number of items with anomalies is found. The anomaly correction system 300 can also, e.g., notify an operator of the anomalies and providing the operator with the tagged image.

Figure 4:
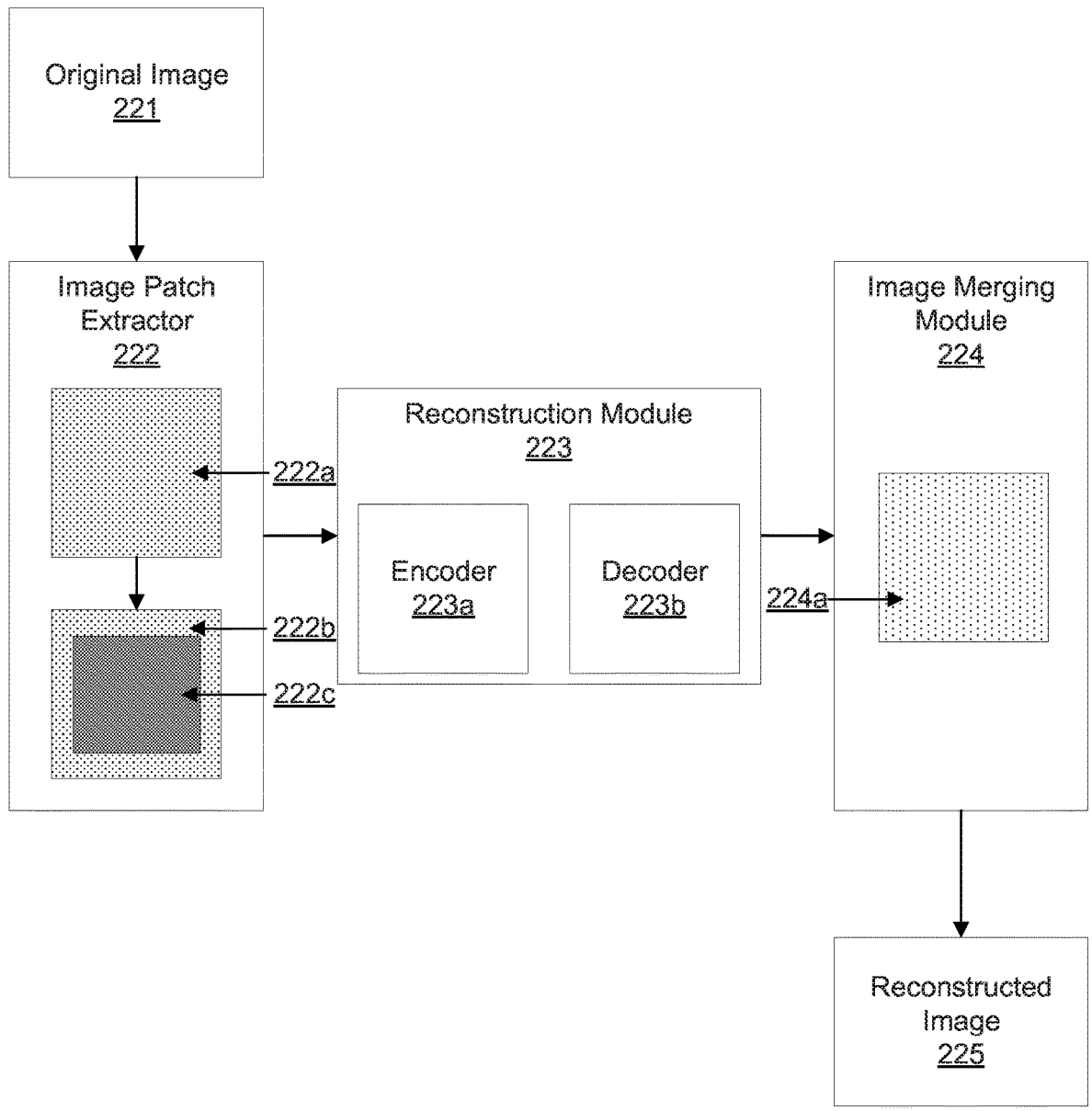
FIG. 4 is a block/flow diagram illustrating a system/method for reconstructing an image for detecting and correcting defects and anomalies, in accordance with the present principles.

Referring now to FIG. 4, a system/method for reconstructing an image for detecting and correcting defects and anomalies is illustratively depicted in accordance with the present principles.

The reconstructor 220 can reconstruct the original image 221 of the item to represent a defectless version of the item by extracting image patches with an image patch extractor 222. The image patch extractor 222 can identify portions of the original image 221 to be reconstructed, such as, e.g., using a grid superimposed on the image. The image patch extractor 222 can then, using a processor, extract a series of image patches 222a from the original image 221, where each image patch 222a in the series is a different portion of the original image 221 according to the identified portions of the original image 221. To facilitate reconstruction of each image patch 222a, a region 222c in each image patch 222a is blacked-out or otherwise masked to generate a partially masked image patch 222b. In this way, data regarding features of the item in the original image 221 is removed from the image patches 222a so that reconstruction can be performed independent of any features present in corresponding portions of the original image 221.

For each image in the series, a reconstruction module 223 can reconstruct the masked region 222c of each partially masked image patch 222b. The reconstruction module 223 can, therefore, include, e.g., a processing device including a processor, and a storage device such as, e.g., a hard drive, solid state drive, a flash memory or a temporary memory, such as, e.g., a RAM, a buffer, or a cache. To reconstruct the masked region 222c, the reconstruction module 223 can utilize, e.g., an encoder-decoder arrangement stored in the storage device, or other suitable neural network for reconstructing images.

According to aspects of the present invention, the reconstruction module 223 is trained using defectless items of the type being analyzed. Thus, when the reconstruction module 223 reconstructs a masked region 222c for each partially masked image patch 222b of the original image 221, it does so based on defectless training by predicting the contents of the masked region 222c. As a result, the reconstructed portion will appear to be defectless in a reconstructed image patch. By training the reconstruction module 223 with defectless items, training images can be easily found. Thus, training of the reconstruction module 223 is quick and efficient, with a large training set facilitating improved accuracy. Moreover, by reconstructing images to be defectless, types of defects and anomalies do not need to be taken into account, thus reducing the complexity of the reconstruction, improving speed and efficiency of an anomaly detection and tagging system 200.

In embodiments of the present invention, the reconstruction module 223 employs an encoder-decoder arrangement including an encoder 223a and decoder 223b. Accordingly, the partially masked image patch 222b with a masked region 222c is provided to the encoder 223a, which transform the partially masked image patch 222b with a hidden layer to a latent representation in a feature space, such as, e.g., a multidimensional feature space vector. The hidden layer can include an activation function and a weight matrix. The encoder 223a can include one or more hidden layers to arrive at an encoded representation, such as, e.g., the multidimensional feature space vector. In addition to masking features of the image patches 222a, the encoder 423a can be configured to reduce the dimensionality of the representation to further obfuscate any features in unmasked regions of the image patches 223, and thus reduce the risk of anomalies being present in a reconstructed representation of the image patches 223.

The encoded representation can then be decoded by the decoder 223b to generate a predicted image patch 224a. Similar to the encoder 223a, the decoder 223b can use one or more hidden layers to transform the encoded representation to a representation corresponding to an output image by using an activation function and a weight matrix. The activation function and weight matrix of the decoder 223b can be the same or different from the activation function and weight matrix of the encoder 223a.

Because the partially masked image patch 222b includes a masked region 222c, the encoder 223a encodes the partially masked image patch 222b without any data related to any features of the item in the masked region 222c. Thus, the features of the corresponding portion of the item are not encoded in the multidimensional features space vector. As a result, the decoder 223b can then reconstruct the image patch 222a by predicting the masked region 222c without any influence from features of a corresponding portion of the original image 221. Thus, a defectless item can be predicted corresponding to the masked region 222c in an efficient manner.

Because the encoder 223a and decoder 223b have been trained with defectless items, the decoder 223b is trained to predict defectless features. Thus, the predicted image portion includes a reconstructed image patch 224a having no defects or anomalies, even if the corresponding image patch 222a of the original image 221 did have defects or anomalies.

The reconstructed image patch 224a can then be merged back into the original image 221 with the image merging module 224. The image merging module 224 can include, e.g., a processing device including a process, and a storage device such as, e.g., a hard drive, solid state drive, a flash memory or a temporary memory, such as, e.g., a RAM, a buffer, or a cache. The reconstructed image patch 224a will replace the corresponding portion of the original image 221 such that the original image 221 becomes a reconstructed image 225. Alternatively, the reconstructed image patch 224a can be stitched with other previously reconstructed image patches, independent of the original image. Each extracted image patch 222a will be reconstructed by the reconstruction module 223 and merged back into the image with the image merging module 224. Thus, the reconstructed image 225 will be produced with every identified portion replaced with a reconstructed version of that portion. As a result, the reconstructed image 225 will depict a defectless item. The reconstructed image 225 can then be stored, e.g., in a storage device such as, e.g., a hard drive, solid state drive, a flash memory or a temporary memory, such as, e.g., a RAM, a buffer, or a cache.

Figure 5:
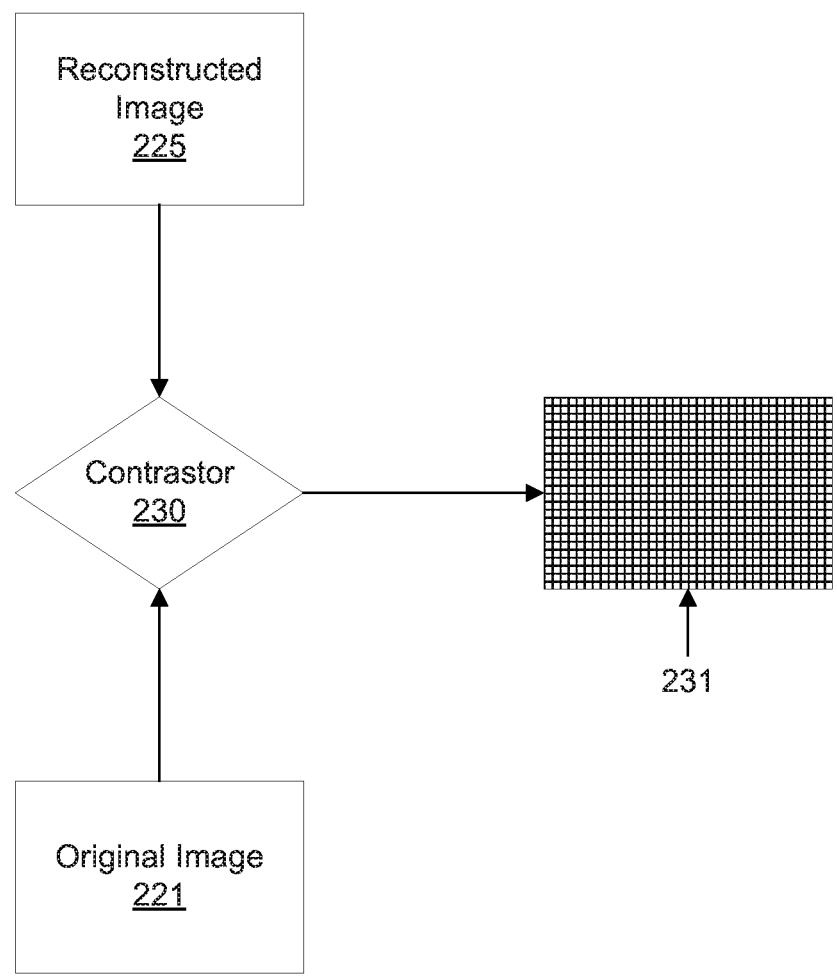
FIG. 5 is a block/flow diagram illustrating a system/method for contrasting a reconstructed image and original image for detecting and correcting defects and anomalies, in accordance with the present principles.

Referring now to FIG. 5, a system/method for contrasting a reconstructed image and original image for detecting and correcting defects and anomalies is illustratively depicted in accordance with the present principles.

A reconstructed image 225 can include an image having a number of portions of an original image 221 reconstructed by a reconstructor 220. Thus, as discussed above, the reconstructed image 225 will depict an item having any defects or anomalies removed by the reconstruction process. The reconstructed image 225 can be contrasted with the original image 221 by a contrastor 230 using, e.g., a processing device including a processor and a storage device, such as, e.g., a hard drive, a solid state drive, a flash memory, a RAM, a buffer or a cache. The contrastor 230 can, e.g., determine a pixel-by-pixel difference between the images to produce an anomaly map 231. Areas of high contrast between the two images will result in a larger difference of pixels at that location. That difference can be mapped to a new image depicting the pixel-by-pixel difference, thus highlighting the anomalies in an anomaly map 231.

Figure 6:
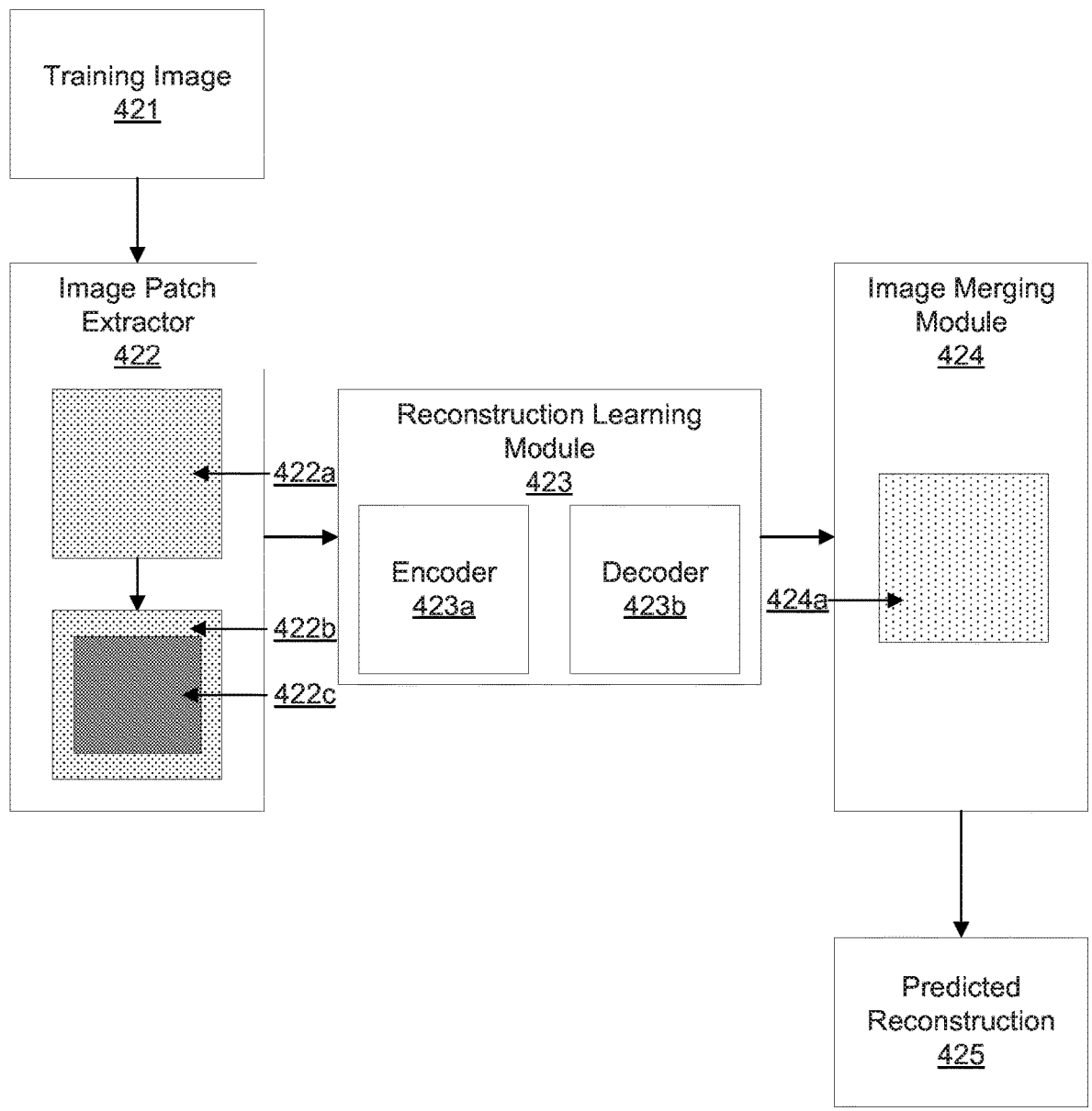
FIG. 6 is a block/flow diagram illustrating a system/method for training a reconstructor for detecting and correcting defects and anomalies, in accordance with the present principles.

Referring now to FIG. 6, a system/method for training a reconstructor for detecting and correcting defective items is illustratively depicted in accordance with the present principles.

A reconstructor can be trained to reconstruct images by training a reconstruction learning module 423 with training images 421. The training images 421 can each include an image of an item of a type to be analyzed by an anomaly detection and tagging system, such as the anomaly detection and tagging system 200 discussed above. Each training image 421 will be defectless, or in other words, "normal". Thus, the reconstruction learning module 423 is training to reconstruct defectless item images. By training the reconstruction training module 423 with defectless items, training images can be easily found. Thus, training of the reconstruction training module 423 is quick and efficient, with a large training set facilitating improved accuracy. Moreover, by reconstructing images to be defectless, types of defects and anomalies do not need to be taken into account, thus reducing the complexity of the reconstruction, improving speed and efficiency of an anomaly detection and tagging system 200.

To train the reconstruction learning module 423, an image patch extractor 422 will extract patches 422a of the training image 421. The image patch extractor 422, including a processing device having a processor, can identify portions of the training image 421 to be reconstructed, such as, e.g., using a grid superimposed on the image. The image patch extractor 422 can then extract a series of image patches 422a from the training image 421, where each image patch 422a in the series is a different portion of the training image 421 according to the identified portions of the training image 421 and temporarily or permanently store the image patches 422a in a cache or a buffer.

A portion of each image patch 422a can be blacked-out or otherwise masked to form a masked region 422c of the image patch 422a to generate a partially masked image patch 422b. This masked region 422c contains no data regarding any features of a corresponding portion of the training image 421. Thus, reconstruction of each partially masked image patch 422b can be performed independent of any features of the training image 421.

For each image in the series, a reconstruction learning module 423 can reconstruct the masked region 422c of each partially masked image patch 422b. The reconstruction learning module 423 can, therefore, include, e.g., a processing device including a processor, and a storage device such as, e.g., a hard drive, solid state drive, a flash memory or a temporary memory, such as, e.g., a RAM, a buffer, or a cache. To reconstruct the masked region 422c, the reconstruction learning module 423 can utilize, e.g., an encoder-decoder arrangement stored in the storage device, or other suitable neural network for reconstructing images.

Accordingly, the partially masked image patch 422b is provided to the encoder 423a, which transforms the masked region 422c with a hidden layer to a latent representation in a feature space, such as, e.g., a multidimensional feature space vector. The hidden layer can include an activation function and a weight matrix. The encoder 423a can include one or more hidden layers to arrive at an encoded representation, such as, e.g., the multidimensional feature space vector. Because the reconstruction learning module 423 is trained with partially masked images 422b, it is unnecessary to reduce the dimensionality of the multidimensional features space vector to below that of an identity function. However, reducing the encoder 423a can be configured to reduce the dimensionality of the representation to further obfuscate any features in unmasked regions of the image patches 423, and thus reduce the risk of anomalies being present in a reconstructed representation of the image patches 223.

The encoded representation can then be decoded by the decoder 423b to generate a predicted image patch 424a. Similar to the encoder 423a, the decoder 423b can use one or more hidden layers to transform the encoded representation to a representation corresponding to an output image by using an activation function and a weight matrix. The activation function and weight matrix of the decoder 423b can be the same or different from the activation function and weight matrix of the encoder 423a.

Because the reconstruction learning module 423 is trained with partially masked images 423, the reconstruction learning module 423 learns reconstruction for image patches by predicting data independent from any preexisting data in the masked portion 422c. Complexity is, therefore, reduced for encoding and decoding, improving the speed and efficiency of the image reconstruction.

The predicted image can then be compared with the input image. An error can be determined according to difference between the input image and predicted image using a loss function. The error can be backpropagate to each hidden layer of the encoder 423a and decoder 423b to update the weight matrices at each layer using a suitable backpropagation process, such as, e.g., a gradient descent method, or a conjugate gradient method, among other backpropagation methods. This process is repeated with multiple training images. The training images will correspond to portions of images of defectless items of the type to be reconstructed. For example, the reconstruction learning module 423 can be trained with manufactured products to reconstruct images of manufactured products. Thus, the encoder-decoder arrangement of the reconstruction learning module 423 will be trained to reconstruct images of defectless items.

While, the training can be performed as an independent process to train the reconstruction learning module 423 prior to implementing the reconstruction learning module 423 as a reconstructing module, such as the reconstruction module 223 discussed above, the reconstruction module can be trained concurrently as a reconstruction learning module 423 with implementing the reconstruction module to reconstruct product images.

Therefore, while reconstructing image portions of a product, a reconstruction module, such as the reconstruction learning module 423 can reconstruct the image patches 422a. The reconstructed image patches 424a can then be merged back into the training image 421 with the image merging module 424. The reconstructed image patch 424a will replace the corresponding image patch 424a of the training image 421 such that the training image 421 becomes a predicted reconstruction 425. Each extracted image patch 422a will be reconstructed by the reconstruction learning module 423 and merged back into the image with the image merging module 424. Thus, the predicted reconstruction 425 can be produced with every identified portion replaced with a reconstructed version of that portion.

The reconstruction version can be contrasted with the original image using a process and system, such as the contrastor 230 and anomaly tagging module 240 described above. If the original image is found to be defect-free, the reconstructed portions can be used to determine an error with, e.g., a loss function, and backpropagate that error to the hidden layers of the reconstruction learning module 423, as discussed above. Thus, the reconstruction learning module 423 can continuously be trained with defect-free product images while concurrently determining if a product has defects.

Figure 7:
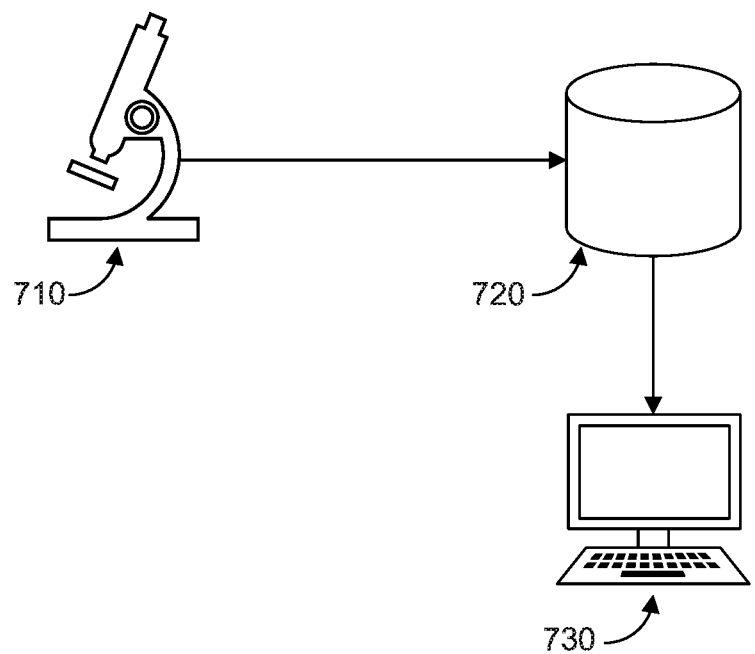
FIG. 7 is a block/flow diagram illustrating a high-level system/method for diagnosing medical anomalies, in accordance with the present principles.

Referring now to FIG. 7, a high-level system/method for diagnosing medical anomalies, in accordance with the present principles is illustratively depicted in accordance with the present principles.

In one embodiment, a medical scanning device 710 generates scans of a person's anatomy, such as, e.g., an X-ray sensor, a magnetic resonance imaging (MRI) device, a computed tomography (CT) scan, a positron emission tomography (PET) scan, optical image, or other scanning device suitable for medical diagnosis. The medical scanning device 710 can, therefore, generate an image of anatomy or physiology. A person's anatomy or physiology can sometimes contain an anomaly that may indicate a disease or condition needing treatment. Thus, the image can be provided to a medical anomaly detection system 720.

The medical anomaly detection system 720 will inspect the anatomy scans to determine if there are any anomalies. Such anomalies can include, e.g., physical signs and symptoms in anatomy and physiology that indicate a medical abnormality including, e.g., a tumor, a blood clot, a broken bone, a dislocation, a fracture, among others. The medical anomaly detection system 720 can determine that an abnormality exists by comparing the scans to a scan that of normal anatomy and physiology. For example, e.g., the medical anomaly detection system 720 can include a machine learning system that is trained with images of medically normal patient anatomy and physiology. By training the system with normal patient scans, the medical anomaly detection system 720 can generate a reconstruction of the anatomy scans that does not contain any abnormalities, and compare the reconstructed version with the original scans to identify differences. The locations of the differences will indicate an anomaly in anatomy or physiology. These differences can, therefore, be identified with the medical anomaly detection system 720.

The identified abnormalities can be communicated to a diagnosis system 730, such as, e.g., a display, computer, or other notification device. Thus, the diagnosis system 730 can notify a doctor of the abnormalities. Therefore, the doctor can easily and quickly find anomalies in a patient's anatomy that may have otherwise gone unnoticed or undetected. Alternatively, the diagnosis system 730 can include a device for automatically administering a medication. For example, where the medical scanning device 710 is an X-ray device, an anomaly may correspond to a broken bone. Thus, the diagnosis system 730 can, e.g., automatically administer a pain killer in response to tagging a bone related anomaly.

Referring now to FIG. 8, a system/method for detecting defects and anomalies with a reconstructor and contrastor is illustratively depicted in accordance with the present principles.

At block 801, extract an image patch from a location on an original image of an item and partially mask the image patch.

The original image can be captured with an imaging device, such as, e.g., a camera, CCD, infrared sensor, LIDAR sensor, or other device for capturing images. The original image will be an image of the item, such as, e.g., a manufactured product, or a part of anatomy, among other items. Occasionally, the item will include defects and anomalies that undesired, such as, e.g., cracks, burrs, protrusions, dents, etc. The image device will capture these anomalies and defects.

Portions of the original image can then be identified to be reconstructed, such as, e.g., using a grid superimposed on the image. The portions are then extracted as a series of image patches from the original image, where each image patch in the series is a different portion of the original image according to the identified portions of the original image. To hide an area of the portions so that the area can be reconstructed, the area can be masked by, e.g., blacking-out, hiding, or otherwise removing the area from subsequent processing.

At block 802, encode the partially masked image patch by transforming the partially masked image patch to a feature space vector using one or more hidden layers of an encoder.

In embodiments of the present invention, the image patch is provided to an encoder, which transform the image patch with a hidden layer to a feature space vector. The hidden layer can include an activation function and a weight matrix. The encoder can include one or more hidden layers to arrive at the feature space vector.

At block 803, reconstruct the partially masked image patch of the item by decoding the feature space vector into a reconstructed patch using one or more hidden layers of a decoder.

The encoded representation can then be decoded by a decoder to generate a predicted image patch that returns the encoded representation back to a representation having the original number of dimensions of the input image patch. Similar to the encoder, the decoder can use one or more hidden layers to transform the encoded representation to a representation corresponding to an output image patch by using an activation function and a weight matrix. The activation function and weight matrix of the decoder can be the same or different from the activation function and weight matrix of the encoder.

Because the encoder encodes a partially masked image portion, the decoder predicts a masked region of the partially masked image portion. Thus, contents, including, e.g., physical or visible features of image patch used as the input image patch, are predicted during decoding by the decoder without influence from any features of the original image of the item. As a result, the output representation including the predicted image patch reconstructs the image patch according to the weight matrix and activation function.

At block 804, merge the reconstructed patch into the location on the original image to generate a reconstructed image.

The reconstructed image patch can then be merged back into the original image. The reconstructed image patch will replace the corresponding portion of the original image such that the original image becomes a reconstructed image. Alternatively, the reconstructed image patch can be stitched with other previously reconstructed image patches, independent of the original image.

Each extracted image portion will be reconstructed and merged back into the image. Thus, the reconstructed image will be produced with every extracted patch replaced with a corresponding reconstructed patch. As a result, the reconstructed image will depict a defectless item. The reconstructed image can then be stored, e.g., in a storage device such as, e.g., a hard drive, solid state drive, a flash memory or a temporary memory, such as, e.g., a RAM, a buffer, or a cache.

At block 805, contrast the reconstructed image with the original to generate an anomaly map that indicates anomalies at locations of differences between the reconstructed image and the original image.

To determine anomalies and defects in the item, the reconstructed image can then be compared to the original image with a contrastor. The contrastor can compare the reconstructed image with the original image by, e.g., performing a pixel-by-pixel difference between the images. However, other contrasting methods are contemplated. Because of the contrasting, the differences between the reconstructed image and original image can be mapped in an anomaly map that represents a degree of difference between the reconstructed image and the original image at each location. The anomaly map can take the form of, e.g., a visual representation, such as an image, or a matrix representation, or by any other suitable representation. As a result, the anomaly map can take the form of separate representation of the item, or it can be overlaid onto the original image to provide both a representation of the actual item, as well as a representation of the anomalies.

At block 806, tag anomalies on the anomaly map to indicate possible anomalies in the item corresponding to the differences between the reconstructed image and the original image.

The anomaly map can then be used to identify anomalies by tagging areas of greatest difference between the reconstructed image and the original image corresponding to the results in the anomaly map. Tagged areas can be determined according to, e.g., an anomaly threshold value that represents degree of difference between the reconstructed image and the original image. If an area has a difference as represented in the anomaly of greater than the anomaly threshold, then that area can be tagged as containing an anomaly on a corresponding location of the item. Thus, item defects and anomalies can be identified. The anomaly tags can be applied to, e.g., the anomaly map, the original image, or both, or as a separate representation, such as, e.g., a list with coordinates.

At block 807, automatically correct the anomalies.

In response to the anomaly map and the anomaly tags, corrective action can be taken. For example, a product having anomalies indicating defects can be automatically removed from a production line, or the entire production line can be automatically stopped. As another possible corrective action, a notification can be provided to an operator via a notification system, such as, e.g., a display or audible alert, such that the operator can take an appropriate action.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A method for detecting and correcting defective products, the method comprising: capturing at least one image of a product with at least one image sensor to generate an original defect-free image of the product; training a model only with the original defect-free image of the product as training data; encoding, with an encoder, each of at least one partly masked portion of an image extracted from the original defect-free image to generate a feature space vector; decoding, with a decoder, the feature space vector to reconstruct the at least one masked portion of the image into a corresponding at least one reconstructed portion by predicting defect-free structural features in each of the at least one masked portion according to hidden layers trained to predict defect-free products; merging each of the at least one reconstructed portion into a reconstructed image defining a defect-free representation of the product; communicating the defect-free representation of the reconstructed image to a contrastor to detect anomalies indicating defects in the product; and contrasting, with the contrastor, the original image with the defect-free representation of the reconstructed image to generate an anomaly map indicating shapes of the defects and locations of difference between the original image and the defect-free representation of the reconstructed image, wherein the encoder transforms the at least one partly masked portion of the image into a reduced dimension vector of numbers to obfuscate any features in unmasked regions of image patches and to reduce a risk of anomalies being present in a reconstructed representation of the image patches.

2. The method as recited in claim 1, wherein the contrastor determines a pixel-by-pixel difference between the defect-free representation of the reconstructed image and the original image.

3. The method as recited in claim 1, wherein the anomaly map includes a matrix of difference values corresponding to differences between the defect-free representation of the reconstructed image and the original image at a plurality of locations on the original image.

4. The method as recited in claim 1, wherein the anomaly map includes an image depicting a difference between the defect-free representation of the reconstructed image and the original image at a plurality of locations on the original image.

5. The method as recited in claim 1, further including tagging locations of difference as anomalies corresponding to defects on the product.

6. The method as recited in claim 1, further including automatically discarding the product according to the detected anomalies.

7. The method as recited in claim 1, further including an image patch extractor to extract at least one image patch and partially mask each of the at least one image patch to generate the at least one masked portion of the original defect-free image.

8. The method as recited in claim 7, wherein the image patch extractor imposes a grid across the original defect-free image, with each area defined by the grid corresponds to a portion to be extracted.

9. The method as recited in claim 1, further including notifying an operator of the anomalies.

10. The method as recited in claim 9, further comprising a display for displaying the original image of the product with tags corresponding to the anomalies.

11. A method for detecting and correcting defective products, the method comprising: extracting, with an image patch extractor, portions of an original image of a product and partially masking each portion to form at least one masked portion; reconstructing, with a reconstructor, the original defect-free image, including: training a model only with the original defect-free image of the product as training data; encoding, with an encoder, each of at least one partly masked portion of an image extracted from the original defect-free image to generate a feature space vector; decoding, with a decoder, the feature space vector to reconstruct the at least one masked portion of the image into a corresponding at least one reconstructed portion by predicting defect-free structural features in each of the at least one masked portion according to hidden layers trained to predict defect-free products; merging the at least one reconstructed portion into a reconstructed image defining a defect-free representation of the product; contrasting, with a contrastor, the original image with the defect-free representation of the reconstructed image to generate an anomaly map indicating shapes of the defects and locations of difference between the original image and the defect-free representation of the reconstructed image; tagging the locations of difference as anomalies corresponding to defects on the product; and notifying, automatically via a display, an operator of the anomalies, wherein the encoder transforms the at least one partly masked portion of the image into a reduced dimension vector of numbers to obfuscate any features in unmasked regions of image patches and to reduce a risk of anomalies being present in a reconstructed representation of the image patches.

12. The method as recited in claim 11, wherein the image patch extractor imposes a grid across the original defect-free image, where each area defined by the grid corresponds to a portion to be extracted.

13. The method as recited in claim 11, further including blacking out an area of the portions to be reconstructed to generate the masked portions.

14. The method as recited in claim 11, wherein the contractor determines a pixel-by-pixel difference between the defect-free representation of the reconstructed image and the original defect-free image.

15. The method as recited in claim 11, wherein the display displays the original defect-free image of the product with tags corresponding to the anomalies.

16. A system for detecting and correcting defective products, the system including: at least one image sensor for capturing at least one image of a product to generate an original image of the product; a reconstructor to reconstruct an original defect-free image of a product by reconstructing partially masked portions of the original defect-free image to be a defectless representation of corresponding portions of the product, the reconstructor including: a model trained only with the original defect-free image of the product as training data; an encoder to encode each of at least one partially masked portion of an image extracted from the original defect-free image to generate a feature space vector; a decoder to decode the feature space vector to reconstruct the at least one portion of the image into a corresponding at least one reconstructed portion by predicting defect-free structural features in each of the at least one portion according to hidden layers trained to predict defect-free products; an image merger to merge each of the at least one reconstructed portion into a reconstructed image defining a defect-free representation of the product; a contrastor for receiving the defect-free representation of the reconstructed image to detect anomalies indicating defects in the product, wherein the contrastor contrasts the original image with the defect-free representation of the reconstructed image to generate an anomaly map indicating shapes of the defects and locations of difference between the original image and the defect-free representation of the reconstructed image; and an anomaly correction system to automatically discard the product according to tagged anomalies, wherein the encoder transforms the at least one partly masked portion of the image into a reduced dimension vector of numbers to obfuscate any features in unmasked regions of image patches and to reduce a risk of anomalies being present in a reconstructed representation of the image patches.

17. The system as recited in claim 16, further including tagging the locations of difference as anomalies corresponding to defects on the product.

18. The system as recited in claim 16, further including a display for displaying the original defect-free image of the product with tags corresponding to the anomalies.

* * * * *